United States Patent
Lu

(10) Patent No.: US 10,617,728 B2
(45) Date of Patent: Apr. 14, 2020

(54) PROBIOTICS AND PREBIOTICS COMPOUND PREPARATION AND PROCESSING METHOD THEREOF

(71) Applicant: Beijing Ebany Biological Medicine Technology Co. Ltd., Beijing (CN)

(72) Inventor: Yi-Bing Lu, Beijing (CN)

(73) Assignee: Beijing Ebany Biological Medicine Technology Co., Ltd., Beijing (CN)

( * ) Notice: Subject to any disclaimer, the term of this patent is extended or adjusted under 35 U.S.C. 154(b) by 9 days.

(21) Appl. No.: 15/989,782

(22) Filed: May 25, 2018

(65) Prior Publication Data

US 2019/0060379 A1 Feb. 28, 2019

(30) Foreign Application Priority Data

Aug. 24, 2017 (CN) .......................... 2017 1 0736057

(51) Int. Cl.

| | | |
|---|---|---|
| *A61K 35/747* | (2015.01) | |
| *A61K 35/745* | (2015.01) | |
| *A61K 31/375* | (2006.01) | |
| *A61K 31/702* | (2006.01) | |
| *A61K 45/06* | (2006.01) | |
| *A61K 31/522* | (2006.01) | |
| *A61P 17/00* | (2006.01) | |
| *A61P 37/00* | (2006.01) | |

(52) U.S. Cl.
CPC .......... *A61K 35/747* (2013.01); *A61K 31/375* (2013.01); *A61K 31/522* (2013.01); *A61K 31/702* (2013.01); *A61K 35/745* (2013.01); *A61K 45/06* (2013.01); *A61P 17/00* (2018.01); *A61P 37/00* (2018.01)

(58) Field of Classification Search
CPC .... A61K 35/747; A61K 45/06; A61K 31/702; A61K 31/375; A61K 35/745
See application file for complete search history.

(56) References Cited

U.S. PATENT DOCUMENTS

| | | | |
|---|---|---|---|
| 7,374,750 B2 * | 5/2008 | Albano ................. | A61K 8/986 424/70.1 |
| 2010/0092429 A1 * | 4/2010 | Nina .................... | A23C 9/1234 424/93.4 |

OTHER PUBLICATIONS

Garaiova et al., European Journal of Clinical Nutrition, 2015, vol. 69, p. 373-379.*
Jaquet et al., International Journal of Food Microbiology, 2009, vol. 130, p. 117-121.*

* cited by examiner

*Primary Examiner* — Kade Ariani
(74) *Attorney, Agent, or Firm* — Wang Law Firm, Inc.

(57) ABSTRACT

A probiotics and prebiotics compound preparation and a processing method thereof are provided. The processing method includes the following processing steps: (1) before production, disinfecting hands of personnel, equipment and tools with alcohol at the concentration of 72 percent; (2) respectively drying stachyose, fructo-oligosaccharide, galactooligosaccharide, isomaltooligosaccharide, *lactobacillus rhamnosus* HN001 and bifidobacterium lactis; (3) mixing 25 to 35 parts of the stachyose, 15 to 25 parts of the fructo-oligosaccharide, 35 to 45 parts of the galactooligosaccharide, 5 to 15 parts of the isomaltooligosaccharide and 0.05 to 0.1 part of caffeine; (4) pasteurizing the mixed saccharide; and (5) respectively adding the lactobacillus rhamnosus HN001 and the *bifidobacterium lactis* Bi-07 into the mixed saccharide according to a ratio of $3\times10^8$ CFU/g. The compound preparation prepared by adopting the method may effectively complete intestinal floras, thereby relieving a burden of allergic dermatitis.

8 Claims, No Drawings

PROBIOTICS AND PREBIOTICS COMPOUND PREPARATION AND PROCESSING METHOD THEREOF

TECHNICAL FIELD

The present application relates to a probiotics and prebiotics compound preparation and a processing method thereof, and more particularly relates to a probiotics and prebiotics compound preparation for preventing and treating eczemas and a processing method thereof.

BACKGROUND ART

Atopic dermatitis (AD) is also called eczema. It is a chronic, recurrent and inflammatory skin disease, and may have a severe influence on the living quality of a children patient and his/her family members. In a clinical research on children allergic dermatitis, researchers gradually find that early emergence of a certain dermatitis symptom of a baby or a child often indicates that other types of allergic dermatitis will occur in the future, and in most cases, AD (eczema) and food allergy are the first symptoms, and then are gradually developed into allergic rhinitis and asthma Some data show that the number of patients under 1 year old is about 50 percent of all patients, and the number of patients under 5 years old is about 90 percent of all patients. The pathogenetic conditions of part of the children patients may be persistent to their adulthoods. The AD has affected 20 to 30 percent of children in developed countries, and in China, the morbidity rate of urban preschool children (1 to 7 years old) in 2002 was 2.78 percent.

At the present, therapies for the AD mainly include a therapy of local external application of anti-inflammatory drugs cooperating with a moisturizer to maintain a skin barrier, and the like, wherein glucocorticoid is a first-line treatment drug, but people have excessive worries about and fears of hormones and doubt about the effect of the moisturizer, which keeps the treatment in a severely nonstandard state all the time. Therefore, it is important to select a product, which is mild and makes the patients feel safe, to intervene the treatment of the eczema.

In recent years, it has been reported at home and abroad that a specific probiotics strain may improve the AD, and it has been proved that prebiotics may effectively proliferate probiotics. Therefore, it is worthy of being expected to combine specific probiotics with specific prebiotics to improve the AD.

According to research at home and abroad in recent years, part of probiotics has a function of improving an allergic constitution, and it is publically known that oligosaccharides proliferate the probiotics.

As a research finds that only individual probiotics may improve the allergic dermatitis such as the eczema, and different oligosaccharides have different proliferation effects on different probiotics, several factors, such as selection of a probiotics strain, the type of an oligosaccharide and a ratio of adding amounts, jointly decide the effect of improving the eczema.

SUMMARY OF THE INVENTION

In view of the shortcomings in the prior art, the present application provides a compound preparation. The compound preparation may effectively help children with incomplete intestinal floras to build their own complete intestinal floras, thereby relieving a burden of allergic dermatitis. Caffeine in a first compound preparation may control development of the allergic dermatitis more quickly, and may quickly improve the allergic dermatitis of children.

To solve the technical problem, the present application adopts the following technical solution: a probiotics and prebiotics compound preparation is provided, including a first compound preparation taken for the first time. The first compound preparation includes components in parts by weight: 25 to 35 parts of stachyose, 15 to 25 parts of fructo-oligosaccharide, 35 to 45 parts of galactooligosaccharide, 5 to 15 parts of isomaltooligosaccharide, 0.05 to 0.1 part of caffeine, *lactobacillus rhamnosus* HN001 at $3\times10^8$ CFU/g and *bifidobacterium lactis* Bi-07 at $3\times10^8$ CFU/g.

In the above technical solution, preferably, the probiotics and prebiotics compound preparation includes a second compound preparation which replaces the first compound preparation after the first compound preparation is taken for at least 5 days, and is used for supplementing prebiotics; and the second compound preparation includes 25 to 35 parts of stachyose, 15 to 25 parts of fructo-oligosaccharide, 35 to 45 parts of galactooligosaccharide and 5 to 15 parts of isomaltooligosaccharide.

In the above technical solution, preferably, the first compound preparation includes 30 parts of the stachyose, 20 parts of the fructo-oligosaccharide, 40 parts of the galactooligosaccharide and 10 parts of the isomaltooligosaccharide.

In the above technical solution, preferably, the second compound preparation includes 30 parts of the stachyose, 20 parts of the fructo-oligosaccharide, 40 parts of the galactooligosaccharide and 10 parts of the isomaltooligosaccharide.

In the above technical solution, preferably, the first compound preparation also includes *lactobacillus acidophilus* NCFM at $3\times10^8$ CFU/g.

In the above technical solution, preferably, the first compound preparation also includes 0.5 to 1.2 parts of vitamin C.

In the above technical solution, preferably, the second compound preparation also includes 0.5 to 1.2 parts of vitamin C.

In the above technical solution, preferably, the first compound preparation also includes 0.5 to 1 part of a sweetening agent.

In the above technical solution, preferably, the second compound preparation also includes 0.5 to 1 part of a sweetening agent.

A processing method of a probiotics and prebiotics compound preparation is provided, including the following steps: (1) before production, disinfecting hands of personnel, equipment and tools with alcohol at the concentration of 72 percent; (2) respectively drying stachyose, fructo-oligosaccharide, galactooligosaccharide and isomaltooligosaccharide with an oligosaccharide dryer through hot air at a temperature of 80 to 100 DEG C. for 15 to 20 s, and respectively drying *lactobacillus rhamnosus* HN001 and *bifidobacterium lactis* through cold air at a temperature of 0 to 20 DEG C.; (3) mixing 25 to 35 parts of the stachyose, 15 to 25 parts of the fructo-oligosaccharide, 35 to 45 parts of the galactooligosaccharide, 5 to 15 parts of the isomaltooligosaccharide and 0.05 to 0.1 part of caffeine; (4) pasteurizing the mixed saccharide, and controlling the pasteurizing temperature to be 85 DEG C. and the pasteurizing time to be 5 min; and (5) adding the *lactobacillus rhamnosus* HN001 and the *bifidobacterium lactis* Bi-07 into the pasteurized mixed saccharide according to a corresponding ratio of $3\times10^8$ CFU/g, and carrying out stirring and mixing for 20 min.

Compared with the prior art, the present application provides the compound preparation. The compound preparation may effectively help the children with incomplete intestinal floras to build their own complete intestinal floras, thereby relieving the burden of allergic dermatitis. The caffeine in the first compound preparation may control the development of the allergic dermatitis more quickly, and may quickly improve the allergic dermatitis of children.

DETAILED DESCRIPTION OF THE INVENTION

For the purpose of making objectives, technical solutions and advantages of the present application clearer, a further detailed description will be made below to the present application in conjunction with embodiments.

A processing method of a probiotics and prebiotics compound preparation includes the following steps: (1) before production, disinfecting hands of personnel, equipment and tools with alcohol at the concentration of 72 percent; (2) respectively drying stachyose, fructo-oligosaccharide, galactooligosaccharide and isomaltooligosaccharide with an oligosaccharide dryer through hot air at a temperature of 80 to 100 DEG C. for 15 to 20 s, and respectively drying lactobacillus rhamnosus HN001 and *bifidobacterium lactis* through cold air at a temperature of 0 to 20 DEG C.; (3) mixing 25 to 35 parts of the stachyose, 15 to 25 parts of the fructo-oligosaccharide, 35 to 45 parts of the galactooligosaccharide, 5 to 15 parts of the isomaltooligosaccharide and 0.05 to 0.1 part of caffeine; (4) pasteurizing the mixed saccharide, and controlling the pasteurizing temperature to be 85 DEG C. and the pasteurizing time to be 5 min; and (5) respectively adding the *lactobacillus rhamnosus* HN001 and the *bifidobacterium lactis* Bi-07 into the mixed saccharide according to a ratio of $3\times10^8$ CFU/g, and carrying out stirring and mixing for 20 min. By the adoption of the processing method, before the production, the hands of personnel, the equipment and the tools are disinfected with the alcohol at the concentration of 72 percent so as to prevent infectious microbes and viruses from being blended into the compound preparation. The stachyose, the fructo-oligosaccharide, the galactooligosaccharide and the isomaltooligosaccharide are dried through the hot air with the temperature of 80 to 100 DEG C. to avoid such a phenomenon that moist has an influence on the efficacy of probiotics or causes caking of the oligosaccharides after the production. The *lactobacillus rhamnosus* HN001 and the *bifidobacterium lactis* are dried through the cold air with the temperature of 0 to 20 DEG C., so that under a condition of keeping the activities of the *lactobacillus rhamnosus* HN001 and the *bifidobacterium lactis*, the phenomenon that moist has an influence on the efficacy of probiotics or causes caking of the oligosaccharides is prevented. The mixed oligosaccharide is pasteurized to prevent infectious microbes from affecting the efficacy of the probiotics.

First experiment: 200 children suffering from eczema were selected, who are from 6 months to 5 years old. With the consents of parents of the 200 children, the 200 children were randomly averagely divided into 8 groups including 7 experiment groups and 1 contrast group in a double-blind manner. 5 g of the caffeine-removed first compound preparation or 5 g of the first compound preparation was added into milk powder which was mixed with warm water at a temperature below 40 DEG C. during feeding of children in the experiment groups every night, but glucose and starch mixed powder of the same dose was added into milk powder during feeding of children in the contrast group. After one month, conditions of the 2 types of groups of children suffering from the eczema were observed, and then comments were made.

For the experiment group 1, the fed caffeine-removed first compound preparation includes 25 parts of stachyose, 15 parts of fructo-oligosaccharide, 35 parts of galactooligosaccharide, 5 parts of isomaltooligosaccharide, *lactobacillus rhamnosus* HN001 at $3\times10^8$ CFU/g and *bifidobacterium lactis* Bi-07 at $3\times10^8$ CFU/g.

For the experiment group 2, the fed caffeine-removed first compound preparation includes 35 parts of stachyose, 25 parts of fructo-oligosaccharide, 45 parts of galactooligosaccharide, 15 parts of isomaltooligosaccharide, *lactobacillus rhamnosus* HN001 at $3\times10^8$ CFU/g, bifidobacterium lactis Bi-07 at $3\times10^8$ CFU/g and *lactobacillus acidophilus* NCFM at $3\times10^8$ CFU/g.

For the experiment group 3, the fed caffeine-removed first compound preparation includes 30 parts of stachyose, 20 parts of fructo-oligosaccharide, 40 parts of galactooligosaccharide, 10 parts of isomaltooligosaccharide, *lactobacillus rhamnosus* HN001 at $3\times10^8$ CFU/g, bifidobacterium lactis Bi-07 at $3\times10^8$ CFU/g, 0.5 part of vitamin C and 0.5 part of a sweetening agent.

For the experiment group 4, the fed caffeine-removed first compound preparation includes 30 parts of stachyose, 20 parts of fructo-oligosaccharide, 40 parts of galactooligosaccharide, 10 parts of isomaltooligosaccharide, *lactobacillus rhamnosus* HN001 at $3\times10^8$ CFU/g, bifidobacterium lactis Bi-07 at $3\times10^8$ CFU/g, *lactobacillus acidophilus* NCFM at $3\times10^8$ CFU/g, 1.2 parts of vitamin C and 1 part of a sweetening agent.

For the experiment group 5, the fed first compound preparation includes 25 parts of stachyose, 15 parts of fructo-oligosaccharide, 35 parts of galactooligosaccharide, 5 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g.

For the experiment group 6, the fed first compound preparation includes 35 parts of stachyose, 25 parts of fructo-oligosaccharide, 45 parts of galactooligosaccharide, 15 parts of isomaltooligosaccharide, 0.1 part of caffeine, *lactobacillus rhamnosus* HN001 at $3\times10^8$ CFU/g, *bifidobacterium lactis* Bi-07 at $3\times10^8$ CFU/g and *lactobacillus acidophilus* NCFM at $3\times10^8$ CFU/g.

For the experiment group 7, the fed first compound preparation includes 30 parts of stachyose, 20 parts of fructo-oligosaccharide, 40 parts of galactooligosaccharide, 10 parts of isomaltooligosaccharide, 0.8 part of caffeine, *lactobacillus rhamnosus* HN001 at $3\times10^8$ CFU/g, *bifidobacterium lactis* Bi-07 at $3\times10^8$ CFU/g, 0.5 part of vitamin C and 0.5 part of a sweetening agent.

SCORAD scores before and after the first experiment (Table I)

| Group | SCORAD score before taking | SCORAD score after taking |
|---|---|---|
| Experiment group 1 | 22.5 ± 11.0 | 14.8 ± 8.9 |
| Experiment group 2 | 21.3 ± 10.5 | 13.6 ± 7.4 |
| Experiment group 3 | 23.0 ± 11.6 | 13.2 ± 7.7 |
| Experiment group 4 | 19.6 ± 8.6 | 12.5 ± 6.6 |
| Experiment group 5 | 21.8 ± 10.3 | 6.3 ± 4.2 |
| Experiment group 6 | 22.6 ± 9.5 | 5.3 ± 3.3 |

-continued

| Group | SCORAD score before taking | SCORAD score after taking |
|---|---|---|
| Experiment group 7 | 24.5 ± 11.5 | 5.8 ± 4.5 |
| Contrast group | 20.2 ± 8.3 | 18.7 ± 9.7 |

Results from Table I found that the first compound preparation without caffeine made a relatively big improvement on the SCORAD indexes of the children suffering from the allergic dermatitis. The caffeine in the first compound preparation might control the development of the allergic dermatitis more quickly, and analysis found that the first compound preparation might quickly improve the allergic dermatitis of the children.

Second experiment: 200 children suffering from eczema were selected, who are from 6 months to 5 years old. With the consents of parents of the 200 children, the 200 children were randomly averagely divided into 10 groups including 9 experiment groups and 1 contrast group in a double-blind manner. 5 g of the first compound preparation or 5 g of the second compound preparation was added into milk powder which was mixed with warm water at a temperature below 40 DEG C. during feeding of children in the experiment groups every night, but glucose and starch mixed powder of the same dose was added into milk powder during feeding of children in the contrast group. After one month, conditions of the 2 types of groups of children suffering from the eczema were observed, and then comments were made.

For the experiment group 1, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g.

For the experiment group 2, the fed first compound preparation includes 30 parts of stachyose, 20 parts of fructo-oligosaccharide, 40 parts of galactooligosaccharide, 10 parts of isomaltooligosaccharide, 0.1 part of caffeine, *lactobacillus rhamnosus* HN001 at $3\times10^8$ CFU/g and *bifidobacterium lactis* Bi-07 at $3\times10^8$ CFU/g; after 2 days, the second compound preparation starting to be fed includes 30 parts of stachyose, 20 parts of fructo-oligosaccharide, 40 parts of galactooligosaccharide, 10 parts of isomaltooligosaccharide and 0.5 part of vitamin C.

For the experiment group 3, the fed first compound preparation includes 30 parts of stachyose, 20 parts of fructo-oligosaccharide, 40 parts of galactooligosaccharide, 10 parts of isomaltooligosaccharide, 0.08 part of caffeine, *lactobacillus rhamnosus* HN001 at $3\times10^8$ CFU/g and *bifidobacterium lactis* Bi-07 at $3\times10^8$ CFU/g; after 3 days, the second compound preparation starting to be fed includes 35 parts of stachyose, 25 parts of fructo-oligosaccharide, 45 parts of galactooligosaccharide, 15 parts of isomaltooligosaccharide, 1.2 parts of vitamin C and 0.5 part of a sweetening agent.

For the experiment group 4, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g; after 4 days, the second compound preparation starting to be fed includes 35 parts of stachyose, 25 parts of fructo-oligosaccharide, 45 parts of galactooligosaccharide, 10 parts of isomaltooligosaccharide, 1.2 parts of vitamin C and 1 part of a sweetening agent.

For the experiment group 5, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g; after 5 days, the second compound preparation starting to be fed includes 30 parts of stachyose, 20 parts of fructo-oligosaccharide, 40 parts of galactooligosaccharide, 10 parts of isomaltooligosaccharide, 1.2 parts of vitamin C and 1 part of a sweetening agent.

For the experiment group 6, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g; after 6 days, the second compound preparation starting to be fed includes 30 parts of stachyose, 20 parts of fructo-oligosaccharide, 40 parts of galactooligosaccharide, 10 parts of isomaltooligosaccharide, 1.2 parts of vitamin C and 1 part of a sweetening agent.

For the experiment group 7, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g; after 7 days, the second compound preparation starting to be fed includes 30 parts of stachyose, 20 parts of fructo-oligosaccharide, 40 parts of galactooligosaccharide, 10 parts of isomaltooligosaccharide, 1.2 parts of vitamin C and 1 part of a sweetening agent.

For the experiment group 8, the fed first compound preparation includes 30 parts of stachyose, 20 parts of fructo-oligosaccharide, 40 parts of galactooligosaccharide, 10 parts of isomaltooligosaccharide, 0.05 part of caffeine, *lactobacillus rhamnosus* HN001 at $3\times10^8$ CFU/g and *bifidobacterium lactis* Bi-07 at $3\times10^8$ CFU/g; after 8 days, the second compound preparation starting to be fed includes 30 parts of stachyose, 20 parts of fructo-oligosaccharide, 40 parts of galactooligosaccharide, 10 parts of isomaltooligosaccharide, 1.2 parts of vitamin C and 1 part of a sweetening agent.

For the experiment group 9, the fed second compound preparation includes 30 parts of stachyose, 20 parts of fructo-oligosaccharide, 40 parts of galactooligosaccharide, 10 parts of isomaltooligosaccharide, 1.2 parts of vitamin C and 1 part of a sweetening agent. SCORAD scores before and after the second experiment (Table II)

| Group | SCORAD score before taking | SCORAD score after taking |
|---|---|---|
| Experiment group 1 | 22.0 ± 11.3 | 6.2 ± 4.2 |
| Experiment group 2 | 23.1 ± 11.2 | 18.6 ± 9.8 |
| Experiment group 3 | 22.6 ± 11.6 | 18.5 ± 9.9 |
| Experiment group 4 | 19.4 ± 9.6 | 17.1 ± 9.5 |
| Experiment group 5 | 19.5 ± 9.9 | 5.3 ± 3.8 |
| Experiment group 6 | 21.4 ± 10.6 | 5.9 ± 4.6 |
| Experiment group 7 | 21.7 ± 9.6 | 5.3 ± 4.4 |
| Experiment group 8 | 19.8 ± 9.5 | 5.1 ± 3.9 |

-continued

| Group | SCORAD score before taking | SCORAD score after taking |
|---|---|---|
| Experiment group 9 | 22.5 ± 9.7 | 6.3 ± 3.6 |
| Contrast group | 21.3 ± 10.3 | 18.8 ± 9.5 |

Results from Table I found that feeding of the second compound preparation after the first compound preparation was fed for 5 days made a relatively big improvement on the SCORAD indexes of the children suffering from the allergic dermatitis. Therefore, the feeding of the second compound preparation after the first compound preparation was fed for 5 days might achieve the basically same therapeutic effect, and also reduce the amounts of the *lactobacillus rhamnosus* HN001 and *bifidobacterium lactis* Bi-07.

The invention claimed is:

1. A probiotics and prebiotics compound preparation, comprising a first compound preparation and a second compound preparation, wherein the first compound preparation is taken by a patient for at least 5 days before the second compound preparation is taken,
    wherein the first compound preparation comprises the following components in parts by weight: 25 to 35 parts of stachyose, 15 to 25 parts of fructo-oligosaccharide, 35 to 45 parts of galactooligosaccharide, 5 to 15 parts of isomaltooligosaccharide, 0.05 to 0.1 part of caffeine, *Lactobacillus rhamnosus* HN001 at $3\times10^8$ CFU/g and *Bifidobacterium lactis* Bi-07 at $3\times10^8$ CFU/g; and
    wherein the second compound preparation comprises the following components in parts by weight: 25 to 35 parts of stachyose, 15 to 25 parts of fructo-oligosaccharide, 35 to 45 parts of galactooligosaccharide, and 5 to 15 parts of isomaltooligosaccharide.

2. The probiotics and prebiotics compound preparation of claim 1, wherein the first compound preparation includes 30 parts of the stachyose, 20 parts of the fructo-oligosaccharide, 40 parts of the galactooligosaccharide, and 10 parts of the isomaltooligosaccharide.

3. The probiotics and prebiotics compound preparation of claim 1, wherein the second compound preparation includes 30 parts of the stachyose, 20 parts of the fructo-oligosaccharide, 40 parts of the galactooligosaccharide, and 10 parts of the isomaltooligosaccharide.

4. A probiotics and prebiotics compound preparation, comprising a first compound preparation and a second compound preparation, wherein first compound preparation is taken by a patient for at least 5 days before the second compound preparation is taken,
    wherein the first compound preparation comprises the following components in parts by weight: 25 to 35 parts of stachyose, 15 to 25 parts of fructo-oligosaccharide, 35 to 45 parts of galactooligosaccharide, 5 to 15 parts of isomaltooligosaccharide, 0.05 to 0.1 part of caffeine, *Lactobacillus rhamnosus* HN001 at $3\times10^8$ CFU/g, *Bifidobacterium lactis* Bi-07 at $3\times10^8$ CFU/g and *Lactobacillus acidophilus* NCFM at $3\times10^8$ CFU/g; and
    wherein the second compound preparation comprises the following components in parts by weight: 25 to 35 parts of stachyose, 15 to 25 parts of fructo-oligosaccharide, 35 to 45 parts of galactooligosaccharide, and 5 to 15 parts of isomaltooligosaccharide.

5. The probiotics and prebiotics compound preparation of claim 1, wherein the first compound preparation further comprises 0.5 to 1.2 parts of vitamin C.

6. The probiotics and prebiotics compound preparation of claim 1, wherein the second compound preparation further comprises 0.5 to 1.2 parts of vitamin C.

7. The probiotics and prebiotics compound preparation of claim 1, wherein the first compound preparation further comprises 0.5 to 1 part of a sweetening agent.

8. The probiotics and prebiotics compound preparation of claim 1, wherein the second compound preparation further comprises 0.5 to 1 part of a sweetening agent.

* * * * *